United States Patent [19]

Harris

[11] Patent Number: 4,895,970

[45] Date of Patent: Jan. 23, 1990

[54] POLY(ALKYLENE CARBONATE) MONOAHLS AND POLYAHLS USEFUL AS SURFACTANTS

[75] Inventor: Robert F. Harris, Midland, Mich.

[73] Assignee: The Dow Chemical Company, Midland, Mich.

[21] Appl. No.: 223,462

[22] Filed: Jul. 22, 1988

Related U.S. Application Data

[63] Continuation of Ser. No. 885,118, Jul. 14, 1986, abandoned.

[51] Int. Cl.$^4$ ............................................. C07C 154/00
[52] U.S. Cl. ...................................................... 558/248
[58] Field of Search ......................................... 558/248

[56] References Cited

U.S. PATENT DOCUMENTS

| | | | |
|---|---|---|---|
| 3,332,980 | 7/1967 | Leary et al. | 558/248 |
| 3,632,828 | 1/1972 | Frevel et al. | 558/248 |
| 4,222,954 | 9/1980 | Cuscurida et al. | 558/248 |
| 4,330,481 | 8/1980 | Timberlake et al. | 558/248 |
| 4,353,834 | 10/1982 | Langdon | 558/248 |
| 4,382,014 | 5/1983 | Sakai et al. | 558/248 |
| 4,415,502 | 11/1983 | Timberlake et al. | 558/248 |
| 4,488,982 | 12/1984 | Cuscurida et al. | 558/248 |
| 4,504,418 | 3/1985 | Langdon | 558/248 |
| 4,686,273 | 8/1987 | Harris | 558/248 |
| 4,686,274 | 8/1987 | Harris et al. | 558/248 |
| 4,709,069 | 11/1987 | Harris | 558/248 |
| 4,745,162 | 5/1988 | Harris | 558/248 |

*Primary Examiner*—Mary C. Lee
*Assistant Examiner*—Robert C. Whittenbaugh

[57] ABSTRACT

Poly(alkylene carbonate) monoahls and polyahls useful as non-ionic surfactants having a poly(alkylene carbonate) backbone are prepared by reacting an oligomeric poly(alkylene carbonate) with a compound having mono- or difunctional active hydrogen moieties, such as alcohols, carboxylic acids, mercaptans, amides, primary or secondary amines, or substituted phenols, in the presence of a catalyst under transesterification conditions. Novel modified poly(alkylene carbonate)monoahls and polyahls are prepared by reactions of mercaptans with poly(alkylene carbonate)polyahls.

12 Claims, No Drawings

POLY(ALKYLENE CARBONATE) MONOAHLS AND POLYAHLS USEFUL AS SURFACTANTS

CROSS-REFERENCE TO RELATED APPLICATION

This is a continuation of application Ser. No. 885,118, filed July 14, 1986 now abandoned.

BACKGROUND OF THE INVENTION

1. Field of the Invention

This invention relates to a method for preparing poly(alkylene carbonate) monoahls and/or polyahls useful as surfactants or functional fluids and to novel monoahls and/or polyahls based on alkyl or aryl mercaptans or their alkoxylate derivatives. This invention also relates to poly(alkylene carbonate) polyahls.

2. Description of the Background

Poly(alkylene carbonate) polyahls are randomized polymers containing a plurality of carbonate moieties and a plurality of active hydrogen moieties and, optionally, other moieties such as di- and higher polyalkyleneoxy units. An alkylene carbonate moiety is a repeating unit comprising an alkylene group bound to a carbonate moiety. Poly(alkylene carbonate) polyahls are known to be useful as surfactants.

Surfactants are compounds that reduce the surface tension when dissolved in water or water solutions, or which reduce the interfacial tension between two liquids, or between a liquid and a solid (see, for example, Nonionic Surfactants edited by M. J. Schick, Marcel Dekker, Inc., New York, 1967). Functional fluids are polyglycol-based fluids such as lubricants, hydraulic fluids, brake fluids, and compressor fluids (see, for example, Kirk-Othmer 12: 719; ibidem., 18: 633).

A variety of surfactants have been prepared by Langdon and described in a series of patents. U.S. Pat. No. 4,072,704 describes the coupling of polyethylene glycols and polypropylene glycols with either dialkyl carbonates or formaldehyde to give materials with surface active properties. In U.S. Pat. No. 4,353,834 it is described how long chain amides or sulfonamides have been coupled with hydrophilic polyglycols using dialkyl carbonates or esters of dicarboxylic acids to give materials with surface active properties. This work was extended in U.S. Pat. No. 4,504,418 to include polyoxyalkylene polymers and monofunctional aliphatic, aromatic or aliphatic-aromatic alcohols coupled by alkyl carbonates or esters of dicarboxylic acids to give materials with surface active properties.

U.S. Pat. No. 4,330,481 to Timberlake et al. describes the preparation of surfactants by reacting alcohols or alcohol ethoxylates with ethylene carbonate. These products are then further reacted with ethylene oxide to produce different surface active materials as reported in U.S. Pat. No. 4,415,502. The preparation of surfactants and functional fluids by reacting alcohols, phenols or carboxylic acids (or their alkoxylated derivatives) with alkylene carbonates or alkylene oxides and carbon dioxide is described in U.S. Pat. No. 4,488,982 to Cuscurida.

U.S. Pat. No. 4,382,014 to Sakai et al. describes the preparation of surface active materials by reacting alcohols, carboxylic acids or primary or secondary amines containing four or more carbon atoms or substituted phenols with alkylene carbonates in the presence of an ate-complex of a metal of Group II, III or IV of the Periodic Table having at least two alkoxy groups.

Low molecular weight polyoxyethylene glycol monomethyl ethyls have been coupled using phosgene or alkyl carbonates to give materials useful in formulating brake fluids and as synthetic lubricants, as disclosed in U.S. Pat. No. 3,632,828. The coupling of monofunctional alcohols, phenols or their ethoxylated derivates using diphenyl carbonate to give surfactants is disclosed in U.S. Pat. No. 3,332,980.

Some poly(alkylene carbonate) polyahl nonionic surfactants of the general type produced by the method of the invention have been made by various procedures, including reacting alcohols with cyclic alkylene carbonates and reacting alcohols with alkylene oxides and carbon dioxide. However, before the present invention poly(alkylene ether carbonate) polyahls have never been used as the carbonate source in preparing carbonate-containing surfactants.

Moreover, carbonate-containing surfactants based on alkyl or aryl mercaptans or their alkoxylate derivatives, which comprise a further part of this invention, are novel.

SUMMARY OF THE INVENTION

The present invention provides a novel process for preparing modified poly(alkylene carbonate) monoahls and/or polyals which are non-ionic surfactants and/or functional fluids containing a poly(alkylene carbonate) backbone.

In one aspect of this invention, poly(alkylene carbonate) polyahls are contacted with monoahls or diahls as hereinafter defined under conditions effective to form the modified poly(alkylene carbonate) monoahls and/or polyahls invoking the reaction of an active hydrogen moiety of the monoahl or diahl with a carbonate moiety of the poly(alkylene carbonate) polyahl. Through this modification, compounds having active hydrogen moieties become bonded to the polyahl backbone to form products having molecular weights between those of the starting reactants.

In a second aspect of this invention, poly(alkylene carbonate) polyahls are contacted with difunctional oleophilic compounds having active hydrogen moieties selected from aliphatic diols, dicarboxylic acids, dimercaptans and primary diamines or secondary diamines having four or more carbon atoms under conditions effective to form the modified poly(alkylene carbonate) polyahls. These oleophilic compounds can have different active hydrogen moieties such as amino alcohols, amino acids, mercaptoalcohols, mercaptoacids and mercaptoamines, although others may also be present. As a result of this modification, the difunctional active hydrogen moieties become bonded to the polyahl backbone to form products having molecular weights between, or intermediate to, those of the starting reactants.

The surfactant properties of the products, i.e., the modified poly(alkylene carbonate) monoahls and/or polyahls, can be varied by varying the molecular weight and the backbone structure of the poly(alkylene carbonate) polyahl, the length of the alkyl substituents on the monoahls and diahls, the type of active hydrogen moieties on the monoahls and diahls and the molar ratio of the reactants. Different surfactant compounds can be produced by further reacting the modified products with alkylene oxides or by first reacting the monofunctional or difunctional active hydrogen moieties with alkylene oxides before modification.

In still another aspect, the present invention provides a novel composition of matter that is formed by reacting monofunctional $C_{1-20}$ aliphatic, or $C_{5-20}$ cycloaliphatic or $C_{6-24}$ aryl mercaptans with poly(alkylene carbonate) polyahls or by reacting dimercaptans, mercaptoalchols, mercaptoacids or mercaptoamines with poly(alkylene carbonate) polyahls.

In yet a further aspect, the invention provides a novel process, by which the aforementioned novel compositions of matter may be prepared by reacting alkyl mercaptans with polyalkylene carbonates, or, alternatively, with alkylene oxides and carbon dioxide.

The carbonate backbone in the non-ionic surfactants prepared by the present method can be degraded by bases, strong acids or by biodegradation. Accordingly, they will be degraded naturally and will not persist in the environment, which is an advantageous characteristic that is required by law in many localities.

DETAILED DESCRIPTION OF THE INVENTION

The process of the invention provides non-ionic surfactants, many of which have physical and chemical properties similar to those prepared by prior art methods. Alkylene carbonates are not, however, required as reactants. Rather, poly(alkylene carbonate) polyahls are made from alkylene oxides and carbon dioxide, and then converted to non-ionic surfactants. One of the starting materials useful in the process of this invention is poly(alkylene carbonate) polyahls.

Poly(alkylene carbonate) polyahls are randomized polymers having a plurality of carbonate moieties and a plurality of active hydrogen moieties, and optionally, other moieties such as di- and higher poly-alkyleneoxy units. An alkylene carbonate moiety is a repeating unit which has an alkylene group bound to a carbonate moiety. An active hydrogen moiety is a moiety containing a hydrogen atom which because of its position in the moiety displays significant activity according to the Zerewitnoff test described by Kohle, J.Amer.Chem.Soc., 493181 (1927). Illustrative of such active hydrogen moieties are —COOH, —OH, —NH$_2$, —NH—, —CONH$_2$, —SH and —CONH—, although other reactive H-containing moieties may also be used. Alkyleneoxy moiety refers herein to a repeating unit which has an alkylene group bound to oxygen. Alkylene carbonate and alkyleneoxy moieties may be respectively represented by the following formulae:

$$+C(R^2)_2-C(R^2)_2-OCO+\!\!\!\!\!\!\!\!\!\underset{O}{\overset{\|}{}}$$

and $$+C(R^2)_2-C(R^2)_2-O+$$

wherein $R^2$ is as hereinafter defined.

Preferred poly(alkylene carbonate) polyahls are random polyols represented by the formula:

$$R^1[X+C(R^2)_2C(R^2)_2O\overline{)_y}+C(R^2)_2C(R^2)_2OCO\overline{)_x}+R^1(XA)_n-\overline{1}\overline{)_z}H]_n \quad (I)$$

wherein $R^1$ is separately in each occurrence an n-valent hydrocarbon radical or hydrocarbon radical which contains one or more heteroatoms of the group consisting of O, N and S;

$R^2$ is separately in each occurrence hydrogen, halogen, nitro, cyano, $C_{1-20}$ hydrocarbyl substituted with hydrogen or one or more of the group consisting of halo, cyano, nitro, thioalkyl, tert-amino, alkoxy, $C_{6-20}$ aryloxy, $C_{7-24}$ aralkoxy, carbonyldioxy($C_{1-20}$) alkyl, carbonyl-dioxy($C_{6-24}$)aryl, carbonyldioxy($C_{7-24}$)aralkyl, $C_{1-24}$ alkoxycarbonyl, $C_{6-24}$ aryloxycarbonyl, $C_{7-24}$ aralkoxy-carbonyl, $C_{1-20}$ alkylcarbonyl, $C_{6-24}$ arylcarbonyl, $C_{7-24}$ aralkylcarbonyl, $C_{1-20}$ alkylsulfinyl, $C_{6-24}$ aryl-sulfinyl, $C_{7-24}$ aralkylsulfinyl, $C_{1-24}$ alkylsulfonyl, $C_{6-24}$ arylsulfonyl and $C_{7-24}$ aralkylsulfonyl;

X is separately in each occurrence S, O, NH,

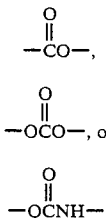

$$-\overset{O}{\overset{\|}{C}}O-,$$

$$-O\overset{O}{\overset{\|}{C}}O-, \text{ or}$$

$$-O\overset{O}{\overset{\|}{C}}NH-;$$

A is separately in each occurrence

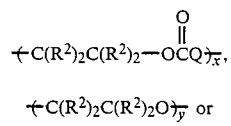

$$+C(R^2)_2C(R^2)_2-OCQ\overline{)_x},$$

$$+C(R^2)_2C(R^2)_2O\overline{)_y} \text{ or}$$

combinations thereof or a covalent bond;

Q is separately in each occurrence O, S or NH provided that all carbonate moieties are not terminal since terminal carbonate moieties are unstable and form OH moieties by elimination of $CO_2$;

n is separately in each occurrence an integer of from 1 to 25;

x is separately in each occurrence an integer of from 1 to 40;

y is separately in each occurrence an integer of from 1 to 120; and z is separately in each occurrence an integer of from 0 to 5.

A more preferred class of poly(alkylene carbonate) polyahls are poly(alkylene carbonate) polyols generally corresponding to the aforementioned formula wherein $R^1$, $R^2$ and n are as previously defined;

X is oxygen;

x is separately in each occurrence an integer of from 5 to 15; and z is an integer of from 0 to 2; provided that the ratio of y to x is from 1:1 to 3:1.

In the hereinbefore-defined formulae, $R^1$ is preferably a $C_{1-24}$ aliphatic or $C_{6-24}$ cycloaliphatic hydrocarbon containing one or more oxygen, nitrogen or sulfur moieties; more preferably $R^1$ is an n-valent $C_{1-18}$ alkane or $C_{6-18}$ cycloalkene substituted with hydrogen or one or more oxygen, nitrogen or sulfur moieties, even more preferably $R^1$ is an n-valent $C_{1-10}$ alkane substituted with hydrogen or one or more oxygen moieties.

$R^2$ is preferably hydrogen, $C_{1-20}$ alkyl, $C_{1-20}$ haloalkyl, $C_{1-20}$ alkenyl or phenyl; $R^2$ is more preferably hydrogen, $C_{1-3}$ alkyl, $C_{2-3}$ alkenyl, or phenyl; $R^2$ is even more preferably hydrogen, methyl or ethyl; $R^2$ is still more preferably hydrogen or methyl, and most preferably, hydrogen.

X is preferably X, O or NH, and most preferably O. Preferably, n is an integer of 1 to 10, inclusive; more preferably, 1 to 5, inclusive; and most preferably n is 1 or 2.

For the purposes of this invention, it is understood that various hydrocarbon moieties such as alkyl, cycloalkyl, aryl, alkylene, acylene, etc. can be inertly substituted with such moities as halo, alkoxy, nitrile and other substituents which do not interfere with the modification reaction.

As used herein, the term "polyahl" includes any polyfunctional compound having on average more than 1 active hydrogen moiety as defined hereinbefore. Specifically included within the definition of polyahl are polyols, polyamines, polyamides, polymercaptans, polyacids and combinations thereof. However, other polymers containing active hydrogens as described hereinabove may also be used. Examples of polyahls suitable for use in the present invention may be found in U.S. Pat. No. 4,465,713 (column 2, lines 42 through column 5, line 17), which is incorporated herein by reference.

Poly(alkylene carbonate) polyahl starting materials useful in this invention are prepared by any method known in the art, such as the condensation of an alkylene carbonate, carbon dioxide and an alkylene oxide, or mixtures of an alkylene carbonate, an alkylene oxide and/or $CO_2$, with an organic compound containing one or more active hydrogen atoms (initiator) in the presence of an alkaline catalyst or metal salt of an alkaline compound. Examples of these poly(alkylene carbonate) polyols and methods for preparation of these polyols are contained in U.S. Pat. Nos. 3,896,090, and 3,689,462 to Maximovich, U.S. Pat. No. 3,313,782 to Springmann, U.S. Pat. Nos. 3,248,416, 3,248,415 and 3,248,414) to Stevens and copending application Ser. No. 750,362 filed on July 1, 1985 by the present inventor and now abandoned, which are all incorporated herein by reference. Alternatively, the poly(alkylene carbonate) polyahls can be prepared by reacting a dialkyl carbonate or diaryl carbonate with an initiator with two or more hydroxyl moities (see, for example, U.S. Pat. No. 4,476,293 and U.S. Pat. No. 4,191,705, which are also incorporated herein by reference).

The other starting material, i.e., the modifier or modifying reactant, is a monoahl or a diahl. A "monoahl" is an organic compound having one active hydrogen moiety and a "diahl" is an organic compound having two active hydrogen moieties. When diamines are employed as the diahl, it is required that the amino moieties be separated by at least four carbon atoms to prevent unwanted intramolecular cyclization during modification of the poly(alkylene carbonate) polyahl. Although diamines having any number greater than 4 carbon atoms may be used, such as up to 30 and greater, preferred are those having up to 18 carbon atoms.

Examples of suitable monoahls include alcohols such as methanol, ethanol, propanol as well as phenols such as phenol, butylphenol, and methylnaphthol; primary and secondary monoamines such as butylamine, n-hexylamine, cyclohexylamine, 1-methylheptylamine, dodecylamine, N-butylaniline, tolyl-N-methylamine; mercaptans such as methyl mercaptan, ethyl mercaptan, dodecyl mercaptan and phenyl mercaptan; monoamides such as acetamide, fumaramide acrylamide; carboxylic acids such as acetic acid and stearic acid and the like. Also suitable monoahls are adducts of alkylene oxide and alkyl phenols, alcohols and monocarboxylic acids such as those discussed in U.S. Pat. No. 4,488,982, which is also incorporated herein by reference. Of the monoahls, the alcohols, amines and mercaptans are preferred as modifying agents. However, other monoahls are also contemplated for use in the present invention.

Suitable exemplary diahls include alkylene glycols such as ethylene glycol and propylene glycol as well as poly(ethyleneoxy) glycols and poly(propyleneoxy) glycols and other alkane diols such as 1,6-hexane diol; and 1,4-butane diol. Diamines such as 1,6-diamino hexane and 1,12-diaminododecane, as well as other alkane diamines and dimercaptans such as dimercaptoethane and 1,12-dimercaptododecane, are also suitable diahls. In addition, diacids such as adipic acid and isophthalic and terephthalic acid are suitable, as are diamides such as 1,4-diamido butane, and bisphenols such as bisphenol-A. Other suitable diahls such as diols, diacids and the like are described in U.S. Pat. No. 4,382,014, which is incorporated hereby by reference. Of the diahls, the glycols diamines and dimercaptans are preferred. It is also understood that mixtures of two or more monoahls, two or more diahls or at least one monoahl and at least one diahl can be suitably employed as the modifying reactant. It is further also understood that any monoahl, diahl or mixture thereof compatible with the present reactants may also be used in the practice of this invention.

In the preparation of surfactants, the modifying reactant should have sufficient hydrophobic moieties to render the modified product surface active. Preferably, in such cases the modifying reactant shall have from about 8 to 20 carbon atoms, most preferably from 10 to 18 carbons.

Catalysts are preferably used in the modification of poly(alkylene carbonate) polyahls with the monoahls and/or diahls. These catalysts are advantageously known transesterification alkali metal or alkaline earth metal salt catalysts such as alkali metal hydroxides, alkaline earth metal hydroxides, alkali metal carbonates, alkaline earth metal carbonates, ammonium hydroxide, and ammonium carbonate. However, other salts of alkali metals or alkaline metals can also be used within the context of this invention.

Preferred catalysts for the modification (e.g., transesterification) of the poly(alkylene carbonate) polyahls are hydroxides of metals such as lithium, sodium, potassium, rubidium, cesium, magnesium, calcium, strontium, barium, zinc, aluminum, titanium, cobalt, germanium, tin, lead, antimony, arsenic and cerium, as well as the alkoxides thereof. Examples of other preferred catalysts are alkaline metal carbonates, alkaline earth metal carbonates, ammonium carbonates, alkaline metal borates, alkaline earth metal borates, ammonium borates, hydrocarbyloxy titanates, zinc borate, lead borate, zinc oxide, lead silicate, lead arsenate, litharge, lead carbonate, antimony trioxide, germanium dioxide, cerium trioxide, aluminum isopropoxide and titanium isopropoxide. Examples of other preferred catalysts include salts of organic acids of magnesium, calcium, cerium, barium, zinc and titanium, alkaline metal stannates, alkaline earth metal stannates, and ammonium stannates.

When amines are used as the modifying reactants, they can also function as the catalyst for the modification reaction. Thus, in many cases, an added catalyst does not provide any further advantage when an amine is used as the modifying reactant.

When a catalyst is employed, it it employed in an amount effective to promote the modification reaction at a rate sufficient to provide useful amounts of the modified poly(alkylene carbonate) polyahl within a six hour period. Preferably the catalyst is employed in concentrations in the range from about 0.001 to about 2 weight %, most preferably from about 0.1 to about 0.5 weight %, based on the weight of total starting materials. Excessive amounts of catalyst are not favorable, particularly when used at high temperatures, since they often cause undesirable degradation of the poly(alkylene carbonate) polyahl.

Although the modification process of this invention may be carried out in an inert solvent such as acetone and methylene chloride, it is generally preferred to practice the process in the absence of solvents.

The modifying reactants, i.e., monoahl or diahl, are employed in amounts effective to provide the poly(alkylene carbonate) polyahl with the surface active property when a surfactant is desired, or the required functional properties when a functional fluid is desired. Preferably, the modifying reactant is employed in an amount sufficient to provide an equivalent ratio of the ahl (mono or diahl) moiety of the modifying reactant to the carbonate moiety of the poly(alkylene carbonate) polyahl in the range from about 0.01:1 to about 2:1, more preferably from about 0.1:1 to about 1:1, and still more preferably from about 0.2:1 to about 1:1.

The conditions, e.g., temperature and pressure, used in the process of this invention are those effective to provide the desired modified product within a reasonable period, e.g., about six hours. An artisan can adjust the different conditions in accordance with the reactants employed and the specific characteristics of the random modified polymer desired. Preferably, the temperature is within a range of from about 80° C. to 225° C., more preferably from about 125° C. to about 200° C., and most preferably from about 80° C. to about 175° C. In the case where an amine is employed as the modifying reactant it is desirable to use temperatures from about 80° C. to about 150° C. It is further observed that lower temperatures within the aforementioned ranges should be employed when higher concentrations of catalyst are used. These pressures may be employed in the practice of the present invention. While the pressures employed are most preferably about atmospheric, somewhat higher pressures are often desired when volatile solvents or volatile modifying reactants are employed.

The modified products of the process are recovered as is or can be obtained by extracting with solvents capable of dissolving either the modified product or the reactants but not both. By means of example, solvents for the various starting materials may be employed, which solvents are not solvents for the modified product. The converse is also possible. Solvents useful for the purification of the modified polyahls include liquid alkanes, alcohols and ketones.

The modified products of the process are generally defined as polymers (particularly oligomers) having ether and some carbonate moieties in the backbone of the polymer and the modifying reactant chemically bound to the polymer. While the carbonate moieties are virtually eliminated when very high ratios of the modifying reactant is employed, it is preferred to maintain an average of between about 0.5 to 10 carbonate moieties in each modified polymer molecule. Most preferably, the modified polymer molecule contains an average from 1 to 5 carbonate moieties and about 1 chemically-bound reactant moiety per molecule.

Structurally, the modification of the poly(alkylene carbonate) polyahl with a monoahl at the site of reaction can be represented as follows

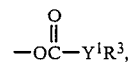

wherein

is the residue of the carbonate moiety

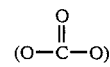

in the poly(alkylene carbonate) polyahl which has reacted with the monoahl $HY^1R^3$ by removal of the active hydrogen moiety of the monoahl. In the above formula, $R^3$ is a monovalent organic radical, preferably $C_{1-20}$ alkyl or $C_{1-20}$ cycloalkyl, $C_{6-24}$ aryl, $C_{7-24}$ aralkyl, still more preferably $C_{1-18}$ alkyl.

$Y^1$ is O, S, NH or $NR^5$, wherein $R^5$ is $C_{1-4}$ alkyl.

In the case of a diahl ($HY^2R^4Y^2H$), the product at the site of reaction may be represented by the formula:

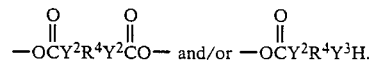

In the foregoing formulae, $R^4$ is a divalent organic radical, preferably a $C_{2-20}$ alkylene, $C_{5-20}$ cycloalkylene, $C_{6-24}$ arylene or $C_{7-24}$ aralkylene, still more preferably $C_{4-12}$ alkylene, and each $Y^2$ is independently O, S, NH, or $NR^5$, preferably O, S and NH; and $Y^3$ is O, S, NH, $NR^5$ or

more preferably O, S and NH.

The entire structure of the modified polymer can thus be represented by substituting the aforementioned reacted carbonate moieties for all or a portion of the carbonate moieties of the poly(alkylene carbonate) polyahl polymer (Formula I) given hereinabove.

As mentioned hereinbefore, it is desirable that only a portion of the carbonate moieties be reacted. Preferably, this portion is the range from 10 to 90 weight % most preferably from about 25 to 50 weight %, of the carbonate moieties of the initial poly(alkylene carbonate) polyahl.

The novel polymers of this invention (including oligomers) which are formed by the reaction of a mercaptan $R^3SH$, or a dimercaptan, $HSR^4SH$, with poly(alkylene carbonate) polyahls are represented by the Formula I hereinabove, wherein all or a significant portion of the carbonate moieties are reacted to form

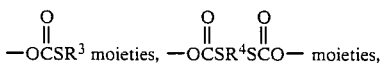

-continued

or $-OCSR^4SH$ moieties, respectively.

SPECIFIC EMBODIMENTS

The following examples are included for illustrative purposes only, and are not meant to limit the scope of the invention or the claims. Unless otherwise stated, all parts and percentages are by weight.

The molecular weights and distribution are determined by size exclusion chromatography (SEC) on Waters Ultrastyragel ® 1000 Å and 10,000 Å columns, arranged in series, using tetrahydrofuran (THF) as the mobile phase and calibrated with narrow molecular weight poly(ethylene glycol) standards using a refractive index detector.

EXAMPLES

EXAMPLE 1: Surfactant From n-Octanol and a Poly(ethylene carbonate) polyol Using a Carbonate:Hydroxyl Ratio of 1.9:1

A poly(ethylene carbonate) diol is prepared from monoethylene glycol and ethylene carbonate (27.6% $CO_2$; 0.00627 mol carbonate/gm; 1943 molecular weight by hydroxyl titration).

A sample of this poly(ethylene carbonate) diol (20.00 g, 0.1254 mol carbonate) is combined with n-octanol (8.66 g, 0.0666 mol) and sodium stannate trihydrate (0.14 g, 0.5%) in a 50 ml, 3-necked flask equipped with overhead stirrer, condenser, thermometer, temperature controller and maintained under a nitrogen atmosphere. The flask is heated to 175° C. and samples are removed periodically for molecular weight determination by size exclusion chromatography (SEC). The results are contained in Table 1 hereinbelow.

TABLE 1

| Sample Number | Conditions | | Peak | $M_n$ | $M_w$ | PDI |
|---|---|---|---|---|---|---|
| 1 | heated | to 175° C. | 163 | 542 | 2558 | 4.71 |
| 3 | 30 min. | at 175° C. | 163 | 487 | 1434 | 2.94 |
| 4 | 1 hr. | at 175° C. | 163 | 455 | 1293 | 2.84 |
| 5 | 1.5 hrs. | at 175° C. | 973 | 431 | 901 | 2.09 |
| 6 | 2 hrs. | at 175° C. | 795 | 429 | 825 | 1.93 |

Equilibrium is established in 1.5-2 hours. Comparative SEC values clearly show the progress of the reactions.

The product (27.2 g) is a pale straw colored, low viscosity liquid.

The results of NMR analysis were as follows:
0.5-1.6 δ (multiplet, $CH_3(CH_2)_6-$, 1.0)
3.6-3.9 δ (multiplet, $-CH_2OCH_2-$, 3.1)
4.0-4.5 δ (multiplet, $-CH_2OCO_2CH_2-$, 1.9).

The product contains 19.7% $CO_2$ and 100% $CO_2$ is retained during reaction.

The surface tension is 35.8 dynes/cm (0.1% aqueous solution).

EXAMPLE 2: Surfactant From n-Octanol and a Poly(ethylene carbonate) polyol Using a Carbonate:Hydroxyl Ratio of 4.0:1

The same poly(ethylene carbonate) diol is used as in Example 1 above. A sample of this poly(ethylene carbonate) diol(20.00 g, 0.1254 mol carbonate) is combined with n-octanol (4.08 g, 0.0314 mol) and sodium stannate trihydrate (0.12 g, 0.5%) in the same apparatus used in Example 1 above. The flask is heated to 175° C. and samples are removed periodically for molecular weight determination by SEC. The results are contained in Table 2 hereinbelow.

TABLE 2

| Sample Number | Conditions | | Peak | $M_n$ | $M_w$ | PDI |
|---|---|---|---|---|---|---|
| 1 | heated | to 175° C. | 3020 | 680 | 2791 | 4.10 |
| 2 | 30 min. | at 175° C. | 2461 | 645 | 2250 | 3.49 |
| 3 | 1 hr. | at 175° C. | 1806 | 600 | 1807 | 3.01 |
| 4 | 1.5 hrs. | at 175° C. | 1628 | 599 | 1528 | 2.55 |
| 5 | 2 hrs. | at 175° C. | 1468 | 571 | 1420 | 2.49 |
| 6 | 3 hrs. | at 175° C. | 1324 | 542 | 1268 | 3.34 |
| 7 | 4.5 hrs. | at 175° C. | 1195 | 571 | 1188 | 2.08 |
| 8 | 6 hrs. | at 175° C. | 973 | 545 | 1117 | 2.05 |

Equilibrium is established in about 3-4 hours. Comparative SEC values clearly show the progress of the reactions.

The product (20.4 g) is a pale straw colored, low viscosity liquid.

The results of NMR analysis are as follows:
0.5-1.6 δ (multiplet, $CH_3(CH_2)_6-$, 1.0)
3.6-3.9 δ (multiplet, $-CH_2OCH_2-$, 7.0)
4.1-4.5 δ (multiplet, $-CH_2OCO_2CH_2-$, 4.2)

The product is 22.0% $CO_2$ and retains 96.5% $CO_2$ during reaction.

Surface tension is 35.7 dynes/cm (0.1% aqueous solution).

EXAMPLE 3: Surfactant From n-Dodecanol and a Poly(ethylene carbonate) polyol Using a Carbonate:Hydroxyl Ratio of 2.5:1

The same poly(ethylene carbonate) diol is used as in Example 1 above. A sample of this poly ethylene carbonate diol) (21.36 g, 0.1339 mol carbonate) is combined with n-dodecanol (9.98 g, 0.0536 mol) in the same apparatus used in Example 1 above. The flask is thoroughly flushed with nitrogen and 0.5 mg titanium isopropoxide is added as catalyst. The flask is heated to 175° C. and samples are removed after 30 minutes and 60 minutes at 175° C. The SEC values are contained in Table 3 hereinbelow.

TABLE 3

| Sample Number | Conditions | Peak | $M_n$ | $M_w$ | PDI |
|---|---|---|---|---|---|
|  | Starting Material | 4086 | 1071 | 3623 | 3.38 |
| 1 | 30 min. at 175° C. | 535 | 471 | 906 | 2.17 |
| 2 | 60 min. at 175° C. | 486 | 406 | 901 | 2.22 |

Equilibrium is established within 30 min at 175° C. The product (31.3 g) is a straw colored, low viscosity liquid.

The results of NMR analysis are as follows:
0.5-1.9 δ (multiplet, $CH_3(CH_2)_{10}-$, 1.0)
3.6-3.9 δ multiplet, $-CH_2OCH_2-$, 3.8)
4.0-4.5 δ (multiplet, $-CH_2OCO_2CH_2-$, 2.5)

The product is 18.9% $CO_2$; 100% $CO_2$ retained during reaction.

The surface tension is 29.0 dynes/cm (0.1% aqueous solution).

EXAMPLE 4: Surfactant From n-Dodecylmercaptan and a Poly(ethylene carbonate) polyol using a Carbonate: Mercaptan Ratio of 2.5:1

A poly(ethylene carbonate) polyol ($\overline{M}n$ 1398) is prepared from ethylene carbonate and diethylene glycol.

A sample of the poly(ethylene carbonate) polyol (18.82 g) is combined with n-dodecylmercaptan (9.32 g) using the same equipment of Example 1. These quantities represent a carbonate to mercaptan molar ratio of 2.5:1. The flask is thoroughly flushed with nitrogen and maintained under a nitrogen atmosphere. Titanium isopropoxide (0.5 ml) is added as catalyst and the content of the reactor are heated to 175° C. Samples are removed periodically for molecular weight determination by SEC. The results are reported in Table 4 hereinbelow.

TABLE 4

| | MOLECULAR WEIGHT DATA | | | | |
|---|---|---|---|---|---|
| Sample Number | Conditions | | Peak | $M_n$ | $M_w$ | PDI |
| 1 | Heated | to 175° C. | 168 | 503 | 1499 | 2.98 |
| 2 | 1 hr. | at 175° C. | 156 | 446 | 967 | 2.18 |
| 3 | 2 hr. | at 175° C. | 168 | 448 | 980 | 2.18 |
| 4 | 3 hr. | at 175° C. | 168 | 434 | 916 | 2.11 |
| 5 | 4 hr. | at 175° C. | 156 | 436 | 907 | 2.08 |

Reaction is completed in 2 to 3 hours. Upon cooling to room temperature, two layers are present. The small upper layer containing some unreacted n-dodecylmercaptan is discarded. The lower product layer a straw colored, viscous liquid containing 19.5% $CO_2$ which displays the following characteristics:

$\overline{M}n$ 429
$\overline{M}w$ 979, and
PDI 2.28.

Proton-NMR data are consistent with the expected product.

Surface tension is 31.5 dynes/cm (0.1% aqueous solution).

EXAMPLE 5: Surfactant from n-Octadecylmercaptan and a Poly(ethylene carbonate)polyol made from Ethylene Oxide and Carbon Dioxide A poly(ethylene carbonate) polyol ($\overline{M}n$ 2076; 27.4 wt % $CO_2$) is prepared from ethylene oxide and carbon dioxide using diethylene glycol as initiator.

A sample of the poly(ethylene carbonate) polyol (100.1 g) is combined with n-octadecylmercaptan (17.19 g) and sodium stannate trihydrate (0.59 g) in a 250 ml flask equipped with a condenser, thermometer, overhead stirrer and maintained under a nitrogen cover. The flask is heated to 175° C. and samples are removed periodically for molecular weight determination. The results obtained are shown in Table 5 hereinbelow.

TABLE 5

| | MOLECULAR WEIGHT DATA | | | | |
|---|---|---|---|---|---|
| Sample Number | Conditions | Peak | $M_n$ | $M_w$ | PDI |
| 1 | Starting material | 4605 | 2076 | 4483 | 2.16 |
| 2 | 2 hr. at 175° C. | 3484 | 1529 | 3402 | 2.23 |
| 3 | 3 hr. at 175° C. | 3246 | 1479 | 3221 | 2.18 |
| 4 | 4 hr. at 175° C. | 1895 | 1486 | 3080 | 2.07 |
| 5 | 5 hr. at 175° C. | 1857 | 1457 | 2908 | 1.99 |

The product (113.5 g) is a white wax. The results of NMR analysis are as follows:

0.7–1.6 δ (multiplet, $CH_3(CH_2)_{16}$—, 1.0);
3.4–3.9 δ (multiplet, —$CH_2OCH_2$—, 30.4);
4.0–4.5 δ (multiplet, —$CH_2OCO_2CH_2$—, 12.5).

Surface tension is 46.7 dynes/cm (0.1% aqueous solution; 23° C.).

EXAMPLE 6: Surfactant from n-Dodecylamine and a Poly(ethylene carbonate) polyol A sample of the same poly(ethylene carbonate) polyol used in Example 5 (100.2 g) and n-dodecylamine (27.80 g) are combined in the same equipment used in Example 6. The flask is heated to 125° C. (no added catalyst) and samples are removed periodically for molecular weight determination. The results are listed in Table 6 hereinbelow.

TABLE 6

| | MOLECULAR WEIGHT DATA | | | | |
|---|---|---|---|---|---|
| Sample Number | Conditions | Peak | $M_n$ | $M_w$ | PDI |
| 1 | Starting material | 4605 | 2076 | 4483 | 2.16 |
| 2 | 1 hr. at 125° C. | 3214 | 1470 | 3147 | 2.14 |
| 3 | 2 hr. at 125° C. | 2014 | 1187 | 2191 | 1.84 |
| 4 | 3 hr. at 125° C. | 1515 | 1092 | 1848 | 1.69 |
| 5 | 4 hr. at 125° C. | 1288 | 1051 | 1707 | 1.62 |
| 6 | 5 hr. at 125° C. | 1288 | 1038 | 1668 | 1.61 |
| 7 | 6 hr. at 125° C. | 1263 | 1019 | 1635 | 1.61 |

Reaction is completed within 3 to 4 hours. The product (122.9 g) is a white wax; 0.189 meq amine/g, 83.9% amine conversion.

The results of NMR spectroscopic analysis are as follows:

0.7–1.6 δ (multiplet, $CH_3(CH_2)_{10}$—, 1.0)
3.3–3.9 δ (multiplet, —$CH_2OCH_2$—, 9.7)
4.0–4.5 δ (multiplet, —$CH_2OCO_2CH_2$—, 3.6)

Surface tension is 31.6 dynes/cm (0.1% aqueous solution; 23° C.).

This example shows that an amine can be used in the process of this invention. The amine also functions as a catalyst. Therefore, no additional catalyst is needed.

EXAMPLE 7: Surfactant from n-Hexadecylamine and a Poly(ethylene carbonate) polyol A sample of the same poly(ethylene carbonate) polyol used in Example 5 (100.3 g) and n-hexadecylamine (19.33 g) are combined in the equipment used in Example 6. The flask is heated to 125° C. and samples are removed periodically for molecular weight determination. The data are contained in Table 7 hereinbelow.

TABLE 7

| | MOLECULAR WEIGHT DATA | | | | |
|---|---|---|---|---|---|
| Sample Number | Conditions | Peak | $M_n$ | $M_w$ | PDI |
| 1 | Starting material | 4605 | 2076 | 4483 | 2.16 |
| 2 | 2 hr. at 125° C. | 4340 | 1952 | 4246 | 2.18 |
| 3 | 3 hr. at 125° C. | 4089 | 1798 | 3940 | 2.19 |
| 4 | 4 hr. at 125° C. | 4089 | 1798 | 3866 | 2.17 |
| 5 | 5 hr. at 125° C. | 3775 | 1695 | 3509 | 2.20 |
| 6 | 6 hr. at 125° C. | 3851 | 1657 | 3661 | 2.20 |

Reaction is complete within 4 to 5 hours. The product (114.4 g) is a white wax; 0.0874 meq amine/g, 86.9% amine conversion.

The results of NMR spectroscopic analysis are as follows:

0.7–1.6 δ (multiplet, $CH_3(CH_2)_{14}$—, 1.0)
3.4–3.9 δ (multiplet, —$CH_2OCH_2$—, 25.6)

4.0–4.5 δ (multiplet, —CH$_2$OC$_2$CH$_2$—, 10.7)

Surface tension is 44.1 dynes/cm (0.1% aqueous solution; 23° C.).

EXAMPLE 8: Surfactant from 1,12-Diaminododecane and a Poly(ethylene carbonate)polyol A sample of the same poly(ethylene carbonate) polyol used in Example 5 (100.5 g) and 1,12-diaminododecane (20.04 g) are combined in the same equipment used in Example 6. The flask is heated to 125° C. and samples are removed periodically for molecular weight determination. The results are tabulated below.

TABLE 8

| Sample Number | Conditions | Peak | $M_n$ | $M_w$ | PDI |
|---|---|---|---|---|---|
| 1 | Starting material | 4605 | 2076 | 4483 | 2.16 |
| 2 | 1 hr. at 125° C. | 1934 | 1046 | 2279 | 1.99 |
| 3 | 2 hr. at 125° C. | 1974 | 1115 | 2223 | 1.99 |
| 4 | 3 hr. at 125° C. | 2098 | 1152 | 2280 | 1.98 |
| 5 | 4 hr. at 125° C. | 2098 | 1184 | 2348 | 1.96 |

The reaction is complete within one hour.

The product (116.6 g) is a white wax; 0.116 meq amine/g, 93.0% amine conversion.

The results of NMR spectroscopic analysis are as follows:

1.2–1.6 δ (singlet, —(CH$_2$)$_{10}$—, 1.0)
3.4–3.9 δ (multiplet, —CH$_2$OCO$_2$CH$_2$—, 5.3)

Surface tension is 52.2 dynes/cm (0.1 aqueous solution; 23° C.).

This example shows that an oleophilic diamine can be used in the process of this invention.

EXAMPLE 9: Surfactant from 1,10-Decanediol and a Poly(ethylene carbonate) polyol A sample of the same poly(ethylene carbonate) polyol used in Example 5 (100.8 g), 1,10-decanediol (17.40 g) and sodium stannate trihydrate (0.59 g) are combined in the same equipment used in Example 5. The flask is heated to 150° C. and samples are removed periodically for molecular weight determination as described in Table 9.

TABLE 9

| Sample Number | Conditions | Peak | $M_n$ | $M_w$ | PDI |
|---|---|---|---|---|---|
| 1 | Starting material | 4605 | 2076 | 4483 | 2.16 |
| 2 | 1 hr. at 150° C. | 2014 | 1175 | 2230 | 1.90 |
| 3 | 2 hr. at 150° C. | 1974 | 1170 | 2241 | 1.91 |
| 4 | 3 hr. at 150° C. | 2014 | 1179 | 2255 | 1.91 |

Reaction is complete within one hour. The product (116.5) is a light straw-colored viscous liquid; Brookfield viscosity, 2570 cps at 23° C.

The results of NMR spectroscopic analysis are as follows:

1.2–2.0 δ (multiplet, —(CH$_2$)$_{10}$—, 1.0)
3.4–3.9 δ (multiplet, —CH$_2$OCO$_2$CH$_2$—, 7.4)

Surface tension is 45.1 dynes/cm (0.1% aqueous solution; 23° C.).

This example shows that an oleophilic diol can be used in the process of this invention.

EXAMPLE 10: Surfactant from Lauric Acid and a Poly(ethylene carbonate) polyol

A sample of the same poly(ethylene carbonate) polyol used in Example 5 (100.5 g), lauric acid (24.04 g) and sodium stannate trihydrate (0.62 g) are combined in the same equipment used in Example 5. The flask is heated to 175° C. and samples are removed periodically for molecular weight determination. Table 10 contains a listing of the data obtained.

TABLE 10

| Sample Number | Conditions | Peak | $M_n$ | $M_w$ | PDI |
|---|---|---|---|---|---|
| 1 | Starting material | 4605 | 2076 | 4483 | 2.16 |
| 2 | 1 hr. at 175° C. | 350 | 1398 | 3822 | 2.73 |
| 3 | 2 hr. at 175° C. | 3851 | 1414 | 3586 | 2.54 |
| 4 | 3 hr. at 175° C. | 3700 | 1431 | 3416 | 2.39 |
| 5 | 4 hr. at 175° C. | 3150 | 1402 | 3262 | 2.32 |

Reaction is complete within about 4 hours. The product (120.2 g) is a light amber semi-solid. Size exclusion chromatography shows that the majority of the lauric acid has reacted.

The results of NMR spectroscopic analysis are as follows:

0.7–1.8 δ (multiplet, CH$_3$(CH$_2$)$_{10}$—, 1.0)
3.4–3.9 δ (multiplet, —CH$_2$OCH$_2$—, 14.2)
4.0–4.5 δ (multiplet, —CH$_2$OCO$_2$CH$_2$—, 5.8)

Surface tension is 31.2 dynes/cm (0.1% aqueous solution; 23° C.).

This example shows that an oleophilic acid can be used in the process of this invention.

It is understood that various other modifications will be apparent to, and can readily by made by, those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A modified poly(alkylene carbonate) polyahl containing at least one thiocarbonate moiety which is the reaction product of a poly(alkylene carbonate) polyahl represented by the formula

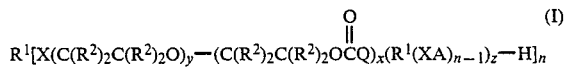

wherein

R$^1$ is separately in each occurrence an n-valent hydrocarbon radical or hydrocarbon radical which contains one or more heteroatoms of the group consisting of O, N and S;

R$^2$ is separately in each occurrence hydrogen, halogen, nitro, cyano, C$_{1-20}$ hydrocarbyl substituted with hydrogen or one or more of the group consisting of halo, cyano, nitro, thioalkyl, tert-amino, C$_{1-20}$ alkoxy, C$_{6-20}$ aryloxy, C$_{7-24}$ aralkoxy, carbonyl-dioxy (C$_{1-20}$) alkyl, carbonyl-dioxy(C$_{6-24}$) aryl, carbonyldioxy(C$_{7-20}$) alkyl, C$_{1-24}$ alkoxycarbonyl, C$_{6-24}$ aryloxycarbonyl, C$_{7-24}$ aralkoxycarbonyl, C$_{1-20}$ alkylcarbonyl, C$_{6-24}$ arylcarbonyl, C$_{7-24}$ aralkylcarbonyl, C$_{1-20}$ alkylsulfinyl, C$_{6-24}$ arylsulfinyl, C$_{7-24}$ aralkylsulfinyl, C$_{1-24}$ alkylsulfonyl, C$_{6-24}$ arylsulfonyl and C$_{7-24}$ aralkylsulfonyl;

X is separately in each occurrence S, O, NH,

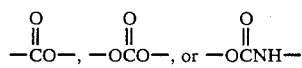

A is separately in each occurrence

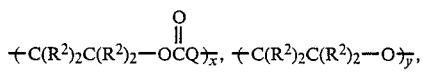

combinations thereof, or a covalent bond;

Q is separately in each occurrence O, S or NH provided that all carbonate moieties are not terminal:

n is separately in each occurrence an integer of from 1 to 25;

x is separately in each occurrence an integer of from 1 to 40;

y is separately in each occurrence an integer of from 1 to 120; and z is separately in each occurrence an integer of from 0 to 5;

and one or more $C_{1-20}$ aliphatic monomercaptans, $C_{5-20}$ cycloaliphatic monomercaptans, $C_{6-24}$ arylmonomercaptans, alkylene dimercaptans having 5-24 carbon atoms, arylene dimercaptans having 6-24 carbon atoms, aralkylene dimercaptans having 7 to 24 carbon atoms, mercaptoalcohols having from about 8 to about 20 carbon atoms, mercaptoacids having from about 8 to 20 carbon atoms or mercaptoamines having from about 8 to about 20 carbon atoms.

2. The modified polyahl of claim 1 wherein

X is oxygen;

x is separately in each occurrence an integer of from 5 to 15; and z is an integer of from 0 to 2; provided that the ratio of y to x is from 1:1 to 3:1.

3. The modified polyahl of claim 2 wherein $R^1$ is an n-valent $C_{1-18}$ alkane or $C_{6-18}$ cycloalkane, substituted with hydrogen or one or more oxygen, nitrogen or sulfur moieties;

$R^2$ is hydrogen, methyl or ethyl;

X is O; and n is 1 or 2.

4. The modified polyahl of claim 1 wherein the modification is with a monomercaptan wherein the modified polyahl at the site of reaction can be represented by the formula

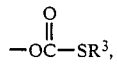

wherein

is the residue of the carbonate moiety

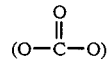

in the poly(alkylene carbonate) polyahl which has reacted with the monomercaptan $HSR^3$ by removal of the active hydrogen moiety of the monomercaptan, and $R^3$ is a monovalent organic radical.

5. The modified polyahl of claim 4 wherein the mercaptan is n-dodecylmercaptan or octadecylmercaptan.

6. The modified polyahl of claim 1 wherein the modification is with a dimercaptan, mercaptoamine, mercaptoalcohol, or mercaptoacid wherein the modified polyahl at the site of the reaction is represented by a formulae selected from the group consisting of

wherein $R^4$ is a divalent organic radical;

$Y^2$ is O, S, NH or $NR^5$, wherein $R^5$ is $C_{1-4}$ alkyl; and $Y^3$ is O, S, NH, $NR^5$ or

7. The modified polyahl of claim 6 wherein $R^4$ is a $C_{2-24}$ alkylene or $C_{5-24}$ cycloalkylene, and $Y^2$ is S, and $Y^3$ is S.

8. A modified poly(alkylene carbonate) polyol having a random structure represented by the formula

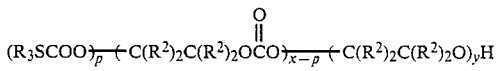

wherein $R^3S$ is a $C_{1-24}$ alkyl, $C_{5-24}$ cycloalkyl or $C_{6-24}$ aryl, $R^2$ is separately in each occurrence hydrogen, $C_{1-20}$ alkyl, p is one to ten, X is one to ten, and y is 2 to 30.

9. The modified polyol of claim 8 wherein $R^3$ is $C_{4-19}$ alkyl.

10. The modified polyol of claim 8 wherein $R^3$ is aryl or aryl substituted with $C_{1-18}$ alkyl.

11. The modified polyol of claim 8 which is surface active.

12. The modified polyol of claim 8, wherein $R^2$ is hydrogen or lower alkyl.

* * * * *